(12) United States Patent
Fischer et al.

(10) Patent No.: US 11,116,467 B2
(45) Date of Patent: Sep. 14, 2021

(54) METHOD FOR RECORDING IMAGE DATA AND MEDICAL IMAGING SYSTEM

(71) Applicant: Siemens Healthcare GmbH, Erlangen (DE)

(72) Inventors: Peter Fischer, Erlangen (DE); Philip Mewes, Nuremberg (DE); Gunter Müller, Heroldsberg (DE)

(73) Assignee: Siemens Healthcare GmbH, Erlangen (DE)

(*) Notice: Subject to any disclaimer, the term of this patent is extended or adjusted under 35 U.S.C. 154(b) by 91 days.

(21) Appl. No.: 16/582,017

(22) Filed: Sep. 25, 2019

(65) Prior Publication Data
US 2020/0093456 A1    Mar. 26, 2020

(30) Foreign Application Priority Data

Sep. 26, 2018    (EP) .................................... 18196788

(51) Int. Cl.
*A61B 6/00*    (2006.01)
*A61B 34/30*    (2016.01)
(Continued)

(52) U.S. Cl.
CPC ............ *A61B 6/541* (2013.01); *A61B 6/4441* (2013.01); *A61B 6/469* (2013.01); *A61B 6/505* (2013.01);
(Continued)

(58) Field of Classification Search
CPC ........... A61B 6/00; A61B 6/541; A61B 6/505; A61B 6/469; A61B 6/5235; A61B 6/4441;
(Continued)

(56) References Cited

U.S. PATENT DOCUMENTS 6,322,567 B1 * 11/2001 Mittelstadt ............ A61B 34/70
606/130
2010/0063514 A1    3/2010 Maschke
(Continued)

FOREIGN PATENT DOCUMENTS

DE    102007007386A1  A1    8/2007
DE    102008022924A1  A1    11/2009
(Continued)

OTHER PUBLICATIONS

European Search Report for European Patent Application No. 18196788.6-1124 dated Mar. 14, 2019.

*Primary Examiner* — Jurie Yun
(74) *Attorney, Agent, or Firm* — Lempia Summerfield Katz LLC

(57) ABSTRACT

A method for recording image data of a moving, (e.g., cyclically moving), region of interest of a patient by a medical imaging system with an X-ray source and an X-ray detector, wherein a robotic device with a kinematic chain of moving components has a tactile connection with the patient, and wherein, the tactile connection is maintained at least for a prespecified period. The method includes acquiring measured values by sensors of the robotic device, evaluating the measured values and forwarding to the medical imaging system, wherein the evaluated measured values include information on the movement and/or position of the region of interest, and irradiation of the region of interest by the radiation source and recording of image data of the irradiated region of interest by the X-ray detector, and wherein the evaluated measured values are used to actuate the imaging system.

13 Claims, 2 Drawing Sheets

(51) Int. Cl.
*B25J 13/08* (2006.01)
*A61B 90/00* (2016.01)
*A61B 17/00* (2006.01)

(52) U.S. Cl.
CPC ............ *A61B 6/5235* (2013.01); *A61B 34/30* (2016.02); *B25J 13/087* (2013.01); *A61B 2017/00858* (2013.01); *A61B 2090/065* (2016.02); *A61B 2090/066* (2016.02)

(58) Field of Classification Search
CPC ....... A61B 6/5288; A61B 6/5294; A61B 6/54; A61B 6/42; A61B 6/52; A61B 6/5264; A61B 34/30; A61B 2090/065; A61B 2090/066; B25J 13/08; B25J 13/087; B25J 13/088
See application file for complete search history.

(56) References Cited

U.S. PATENT DOCUMENTS

| | | |
|---|---|---|
| 2011/0218423 A1 | 9/2011 | Hsieh |
| 2016/0144510 A1 | 5/2016 | Gulhar |
| 2016/0249990 A1 | 9/2016 | Glozman |
| 2017/0020630 A1* | 1/2017 | Johnson ............... A61B 90/361 |
| 2017/0202629 A1 | 7/2017 | Maillet |

FOREIGN PATENT DOCUMENTS

| | | |
|---|---|---|
| DE | 102014224122A1 A1 | 6/2016 |
| EP | 3456280 A1 | 3/2019 |

* cited by examiner

METHOD FOR RECORDING IMAGE DATA AND MEDICAL IMAGING SYSTEM

The present patent document claims the benefit of European Patent Application No. 18196788.6, filed Sep. 26, 2018, which is hereby incorporated by reference.

TECHNICAL FIELD

The disclosure relates to a method for recording image data of a moving, (e.g., cyclically moving), region of interest, a method for recording image data of a moving, (e.g., cyclically moving), region of interest, and a medical imaging system for recording image data.

BACKGROUND

During medical imaging of movable anatomical structures of a patient, inconsistencies frequently occur in the recorded image information due to, for example, respiration, heartbeat, or manipulation on the body. This is in particular problematic in the case of time-lapsed sequential imaging in conjunction with a lack of information on the patient's position at the two recording times. In the case of 2D-2D-3D registration, movement by the patient is particularly critical between the first 2D(1) recording and the second 2D(2) recording. Movement of the patient between the first 2D(1) recording and the second 2D(2) recording, during, for example, the registration of the two recordings to form a 3D volume, results in artifact-cluttered averaging between the 2D(1) recording and the 2D(2) recording or focusing or optimization on either the first 2D(1) recording or the second 2D(2) recording.

Based on the imaging, a subsequent intervention is then subject to similar problems in that any movements of the anatomy render target positions obsolete. For example, in the case of tissue being cut or bone being drilled, in reality, the target position of a cut or drill hole defined by imaging does not remain constant on account of the movement and hence there is a risk that surgeon will miss the real target position. In addition to incorrect diagnoses, this may result in cutting or drilling in the wrong place and considerable undesirable injuries to the patient.

In known cases, to avoid such problems, for example, movement of the patient is suppressed (e.g., by holding the breath, fixing the patient's anatomy) or the patient is tracked by navigation devices or the patient's movement is measured (breathing belt, for example) and then the movement incorporated accordingly in the planning of the recording or evaluation.

SUMMARY AND DESCRIPTION

The scope of the present disclosure is defined solely by the appended claims and is not affected to any degree by the statements within this summary. The present embodiments may obviate one or more of the drawbacks or limitations in the related art.

It is an object of the present disclosure to provide a method for recording image data of a (e.g., cyclically) moving region of interest, which enables the imaging to be as movement independent as possible. A further object of the disclosure is to provide an X-ray device suitable for carrying out the method.

The object is achieved by a method for recording image data of a (e.g., cyclically) moving region of interest, a method for recording image data of a (e.g., cyclically) moving region of interest, and by a medical imaging system.

The method is embodied to record image data of a (e.g., cyclically) moving region of interest of a patient by a medical imaging system, in particular with an X-ray source and an X-ray detector, wherein a robotic device with a kinematic chain of moving components has a tactile connection to the patient, and wherein the tactile connection is maintained at least for a prespecified period, in particular, by conjoint movement of the moving components. In the method, the following acts are performed: acquisition of measured values by sensors of the robotic device, evaluation of the measured values and forwarding to the medical imaging system, wherein the evaluated measured values may include information on the movement and/or position of the region of interest, and recording of image data of the, in particular irradiated, region of interest, in particular in the case of the irradiation of the region of interest by the radiation source, and recording by the X-ray detector, wherein the evaluated measured values are used to actuate the imaging system. Cyclic movements, (for example, respiratory movements or heart movements), or other movements, (for example, movements induced by an intervention), of a patient also exert an influence on the region of interest, e.g., any of the patient's organs (for example, the liver), and also result in (for example, cyclic) movements there, which exert an influence on the image data, for example, in the case of an X-ray recording.

In the case of interventions in which the presence and use of a robotic device with a kinematic chain of moving components is standard, the device may be used not only for the actual intervention, but also for the determination of information on the (e.g., cyclic) movements of a region of interest and hence also to actuate the imaging system. Therefore, targeted use is made of an existing resource, the robotic device, which has a tactile connection with the patient and hence no additional measures or devices need to be provided to measure the movement or position of the region of interest. Overall, it is possible, but not necessary, for the robotic device to be spatially registered to the medical imaging system. The method is in particular suitable for X-ray imaging, but may also be used with other imaging methods, such as magnet resonance imaging or ultrasound imaging.

In one embodiment, the irradiation of the region of interest and the recording of the image data are gated in dependence on the evaluated measured values, in particular, controlled by movement and/or positional data from the region of interest. Herein, the robotic device is used in a simple manner for targeted gating during the imaging. This is particularly advantageous because, on account of the tactile contact, the robotic device is able to determine movements and/or positions particularly accurately. Advantageously, at least one projection recording of the region of interest may be performed at a predetermined time and/or a predetermined phase of the, in particular cyclic, movement of the region of interest. Cyclic movements enable, for example, targeted respiratory gating or cardiac gating to be performed, wherein a predetermined time or a predetermined phase is utilized. With other (e.g., non-cyclic) movements, a resting phase may be used for the imaging.

According to a further embodiment, at least two projection recordings of the region of interest are performed at the same time and/or the same phase of the in particular cyclic movement of the region of interest. The recordings in comparable phases or at the same times of a cyclic movement make it easier to compare the recordings and thus subsequent motion compensation is simplified or may be omitted completely.

The method may be used in the case of registration, such as 2D-2D-3D registration, wherein the two projection recordings are recorded from different projection directions (e.g., angulations of a recording system of the medical imaging system) and used for the 2D-2D-3D registration with a volume image that was recorded previously or has been provided from some other modality. This simplifies the registration and enables it to be performed more accurately. This makes further diagnostic and image processing procedures easier to perform and hence improves patient safety and care.

According to a further embodiment, the recorded image data is processed using the evaluated measured values. The evaluated measured values make processing of the recordings easier. For example, this enables movements to be tracked and corrected accordingly in a simple way.

Advantageously, the measured values are acquired by a force and/or torque and/or position sensor system of the robotic device. Conventional robotic devices with a kinematic chain of moving components possess, (for example, in the region of their joints), sensors of this kind, which may be used for the known positioning of the components.

Advantageously, the robotic device includes at one end an end effector, which is in tactile contact with the patient, e.g., lies on the surface of the patient or the region of interest (e.g., organs) or a bone (for example, spine, femur) of the patient or is connected thereto. For example, in particular in the case of interventional procedures, the end effector may include a toothed sleeve and be in contact with one of the patient's bones (for example, in the case of spine surgery with a vertebral body or pedicle or lamina).

A further variant of the method for recording image data of a moving, (in particular cyclically moving), region of interest of a patient by a medical imaging system, in particular, with an X-ray source and an X-ray detector, wherein a robotic device with a kinematic chain of moving components has a tactile connection with the patient, and wherein the tactile connection is maintained at least for a prespecified period, in particular, by conjoint movement of the moving components includes meanwhile the following acts: recording of image data of the, in particular irradiated, region of interest, in particular in the case of the irradiation of the region of interest by the radiation source and recording by the X-ray detector and acquisition of measured values by sensors of the robotic device, wherein subsequently the measured values are evaluated and forwarded to the medical imaging system, wherein the evaluated measured values may include information on the movement and/or position of the region of interest, and wherein the recorded image data is processed using the evaluated measured values. Therefore, here, the recorded measured values (or information on the movements and or positions of the region of interest) are taken into account in the further image processing in order, for example, to perform motion corrections, reduce or avoid inconsistencies and hence improve diagnostic possibilities. Thus, for example in the case of 2D-2D-3D registration, it is possible for the movement to be corrected in a simple and effective manner and hence for a high-quality outcome to be achieved.

To perform the method, a medical imaging system for the acquisition of image data of a cyclically moving region of interest of a patient is provided including an imaging unit for recording image data from the region of interest, in particular a radiation source for emitting X-rays and an X-ray detector for recording image data of the irradiated region of interest, a control unit for the gated actuation of the (radiation output and the) recording of image data, a robotic device with a kinematic chain of moving components including a force and/or torque and/or position sensor system for acquiring measured values, which may include information on the movement and/or position of the region of interest, wherein the robotic device has a tactile connection with the patient, an evaluation unit for the evaluation of the measured values and a communication link for forwarding the measured values, wherein the medical imaging system is embodied to use the evaluated measured values to actuate the imaging system.

Advantageously, the control unit is embodied to control the irradiation of the region of interest and the recording of the image data gated in dependence on the evaluated measured values.

According to one embodiment, the medical imaging system includes an image processing unit for processing the image data using the evaluated measured values.

In addition, in accordance with a further embodiment, the medical imaging system includes a registration unit for performing a 2D-2D-3D registration between two (2D) projection recordings recorded from different projection directions at the same time and/or the same phase of the cyclic movement of the region of interest and a 3D volume image of the region of interest.

BRIEF DESCRIPTION OF THE DRAWINGS

The disclosure and further advantageous embodiments are explained in more detail below with reference to schematically illustrated exemplary embodiments in the drawing without thereby restricting the disclosure to these exemplary embodiments in which.

DETAILED DESCRIPTION

Figure 3:
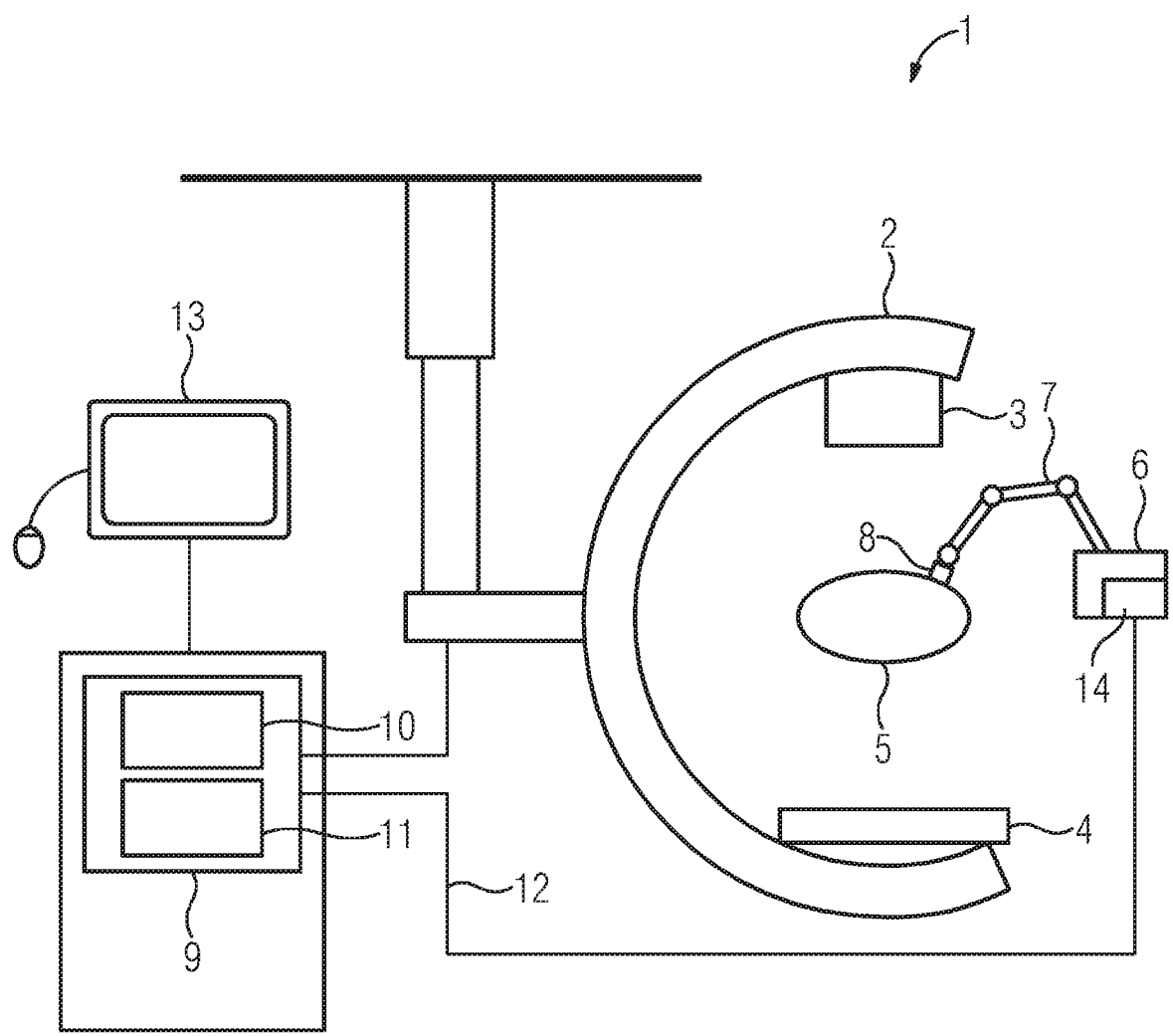
FIG. 3 depicts an example of a medical imaging system for carrying out the method.

FIG. 3 depicts a medical imaging system 1 with a robotic device 6. The medical imaging system 1 includes, for example, as a recording system a C-arm 2 with an X-ray source 3 and an X-ray detector 4, which are embodied to irradiate a region of interest 5 (for example, an organ or body part) of a patient and to record projection images of the irradiated region of interest 5. Herein, the C-arm 2 may be embodied as adjustable or movable so that it is able to record projection images from different projection directions (e.g., angulations). The medical imaging system 1 is actuated by a control unit 9 and also includes a computing unit 10 and an image processing unit 11 with software for processing recorded image data. The medical imaging system 1 also has a communication link 12 to a robotic device 6. The communication link 12 may be wired or wireless.

The robotic device 6 includes a kinematic chain of moving components 7 (for example, arms and joints) and arranged on its free end there is an end effector 8, which may be in contact with the region of interest 5 or another part of the patient. The robotic device 6 may be formed by a robot with articulated arms, such as a light-weight robot or a 6- or 7-axis articulated-arm robot. The end effector may be a toothed sleeve which is, for example, in contact with a vertebral body of the patient for an intervention. The toothing is configured to prevent slippage or breakage of the contact.

In the case of movements or changes of position of the patient, the robotic device may be actuated such that its movement is conjoint with that of the body part with which it is contact with the so that the contact is retained. It is even possible to maintain a corresponding pressure. This may be achieved by force and/or torque regulation. To this end, the moving components 7 of the robotic device include a force and/or torque and/or position sensor system, e.g., at least one such sensor for each moving component. Examples of such robotic devices are, for example, known from the published German application DE 102014224122 A1 or the post-published European application EP 17191039.

The force and/or torque and/or position sensors of the robotic device acquire measured values, which indicate, either directly or indirectly, information or data on the position or movement of the region of interest or the body part to which they are connected. For example, such force or torque sensors are known and are particularly suitable for determining forces and/or torques on the kinematic chain of robotic devices. Herein, either the forces applied are measured directly or values are measured from which it is possible to determine or calculate the force applied in a simple manner. Therefore, the measured values may be evaluated (e.g., processed or converted) in order to provide the position or movement. However, this may be performed very quickly by an evaluation unit 14 (for example, a control unit and/or computing unit of the robotic device).

A medical imaging system 1 of this may be used in combination with a robotic device 6 to carry out the method.

Figure 1:
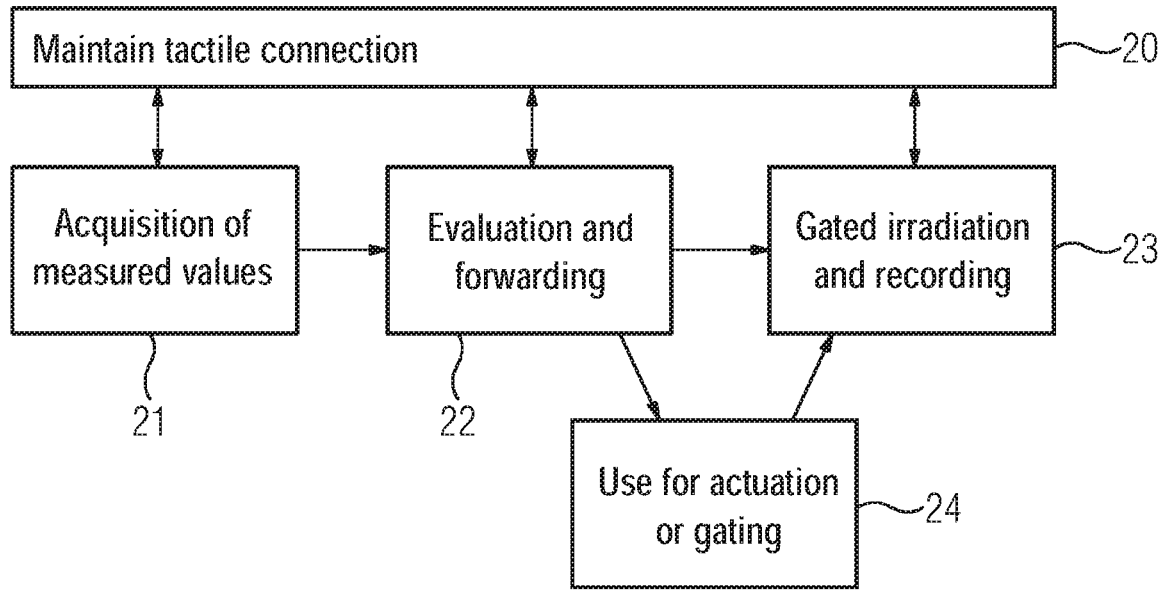
FIG. 1 depicts an example of a sequence of acts of a method.

In a first variant, depicted in FIG. 1, a method is shown with which evaluated measured values with information on the position and/or movement of the patient or the region of interest are used to actuate the imaging of the medical imaging system. Specifically, the information is used to gate the imaging at desired times or phases of (e.g., cyclic) movements of the patient or the region of interest while the robotic device is simultaneously connected to the patient.

In act 20, the robotic device 6, which has a tactile connection with the moving (for example, cyclically moving) patient, the tactile connection is maintained at least for a prespecified period by conjoint movement of the moving components. For example, a robotic device 6, which, for an interventional procedure on bone tissue, is connected to bone tissue of a patient (for example, the spine) by a toothed sleeve as an end effector with the bone may be conjoint with the position of the bone by the force and/or torque and/or position sensor system and thereby stabilized on the bone. Herein, the prespecified period during which the tactile connection is maintained may correspond to the duration of the method or any period specified by a user of the medical imaging system period or be continued until a selectable cancel criterion is reached. The subsequent acts are performed while the tactile connection is maintained. The tactile connection may be with the region of interest or another body part of the patient.

In act 21, the robotic device 6 or the sensor system thereof acquires measured values and, in act 22, these measured values are evaluated and forwarded to the medical imaging system (not necessarily in this order). Herein, the evaluated measured values in particular contain information on the movement and/or position of the region of interest or the patient. Specifically, the measured values may directly or indirectly contain, for example, the active force on the moving components of the robotic device in different directions or the position of the moving components of the robotic device in the case of compliant regulation. The evaluation may be performed by an evaluation unit 14 of the robotic device or also by the medical imaging system. It may take the form that the exact positions of the patient, a body part of the patient or the region of interest is ascertained during a (e.g., cyclic) movement or the (relative or absolute) movement.

In act 23, the information or measurement data or evaluated measurement data (in particular, movement and/or positional data from the region of interest) are then used by the medical imaging system (for example, system control and/or software applications) in order, in act 24, to perform one or more gated X-ray recordings (e.g., irradiation by the X-ray source and acquisition of the radiation influenced by the region of interest by the X-ray detector and conversion into image data). In the simplest case, therefore, respiratory gating or cardiac gating is performed in which a recording is performed at the same times in a plurality of successive phases of the respiration or the heartbeat in order to be able to compare the plurality of resulting projection recordings with one another.

Thus, for example, during 2D-2D-3D registration in which a previously recorded volume image with two projection recordings from different projection directions is registered, a method of this kind is used to record the two projection recordings at the same times in successive respiratory cycles (or cardiac cycles) from different projection directions of the recording system in a gated manner. A particularly exact and precise 2D-2D-3D registration may be performed subsequently. For this purpose, it is possible, but not necessary, for the robotic device to be spatially registered to the medical imaging system. In addition, the information on the movements or positions of the region of interest may also be included in later image processing in order to perform motion compensation and/or avoid or reduce inconsistencies. For example, information on the position may be incorporated in the registration. Thus, for example the respiratory movement of the spine is mainly in the anterior-posterior direction, which is measured by the robotic device and may be taken into account in the registration as a relative transformation.

Thus, the method may enable a robotic device with moving components, which, for a guided intervention, is in contact with the anatomical structures of a patient, to be simultaneously used as an integrated gating triggering device.

Figure 2:
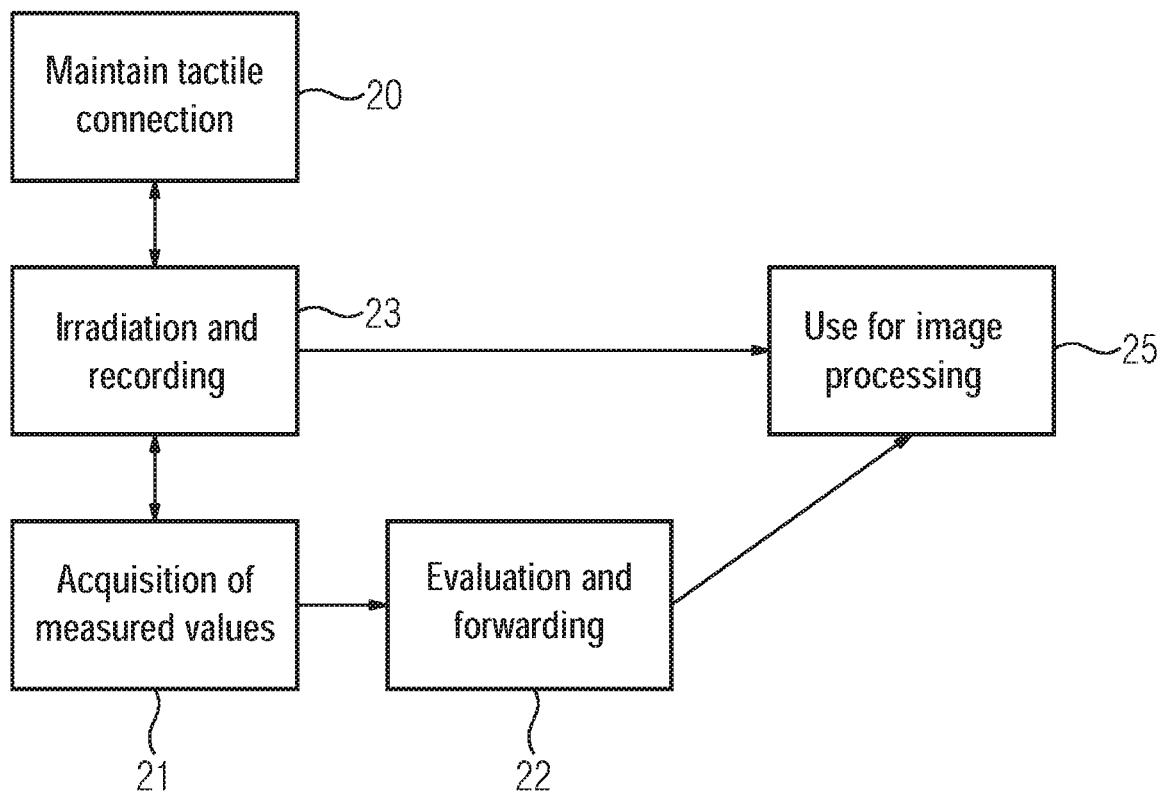
FIG. 2 depicts an additional example of a sequence of acts of a method.

In a second variant, depicted in FIG. 2, a method is shown in which only processing of the recorded image data using evaluated measured values is performed. Here, while the tactile connection is maintained in act 20, simultaneously one or more X-ray recordings are performed in act 23 and corresponding measured values acquired by the sensor system of the robotic device in act 21. The evaluated measured values also contain information on the position and/or movement of the region of interest. This information is forwarded to the medical imaging system (or only evaluated there) and subsequently used further in act 25 for the image processing. For example, the information on the movements or positions of the region of interest may be included in the image processing in order to perform motion compensation and/or avoid or reduce inconsistencies.

According to a further alternative, the medical imaging system may also be used to release or initiate an intervention act in dependence on the current position or movement of the region of interest.

In the case of interventions in which the presence and use of a robotic device with a kinematic chain of moving components is standard, the device may be used not only for the actual intervention, but also for the determination of information on the (e.g., cyclic) movements of a region of interest and hence also to actuate the medical imaging system (for example respiratory gating or cardiac gating).

The disclosure may be briefly summarized as follows: a method for recording image data of a moving, in particular cyclically moving, region of interest of a patient by a medical imaging system with an X-ray source and an X-ray detector, wherein a robotic device with a kinematic chain of moving components has a tactile connection with the patient, and wherein the tactile connection is maintained at least for a prespecified period in particular by conjoint movement of the moving components, and wherein meanwhile the following acts are performed: acquisition of measured values by sensors of the robotic device, evaluation of the measured values and forwarding to the medical imaging system, wherein the evaluated measured values may include information on the movement and/or position of the region of interest, and irradiation of the region of interest by the radiation source and recording of image data of the irradiated region of interest by the X-ray detector, and wherein the evaluated measured values are used to actuate the imaging system.

Although the disclosure was illustrated and described in more detail by the exemplary embodiments, the disclosure is not restricted by the disclosed examples and other variations may be derived herefrom by the person skilled in the art without departing from the scope of protection of the disclosure. It is therefore intended that the foregoing description be regarded as illustrative rather than limiting, and that it be understood that all equivalents and/or combinations of embodiments are intended to be included in this description.

It is to be understood that the elements and features recited in the appended claims may be combined in different ways to produce new claims that likewise fall within the scope of the present disclosure. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

The invention claimed is:

1. A method for recording image data of a moving region of interest of a patient by a medical imaging system comprising an X-ray source and an X-ray detector, the method comprising:
    positioning a robotic device having a kinematic chain of moving components against the patient to provide a tactile connection having a pressure against the patient, wherein the tactile connection is maintained for at least a prespecified period by force regulation and/or torque regulation;
    acquiring measured values by sensors of the robotic device positioned against the patient, wherein the measured values are acquired by a force sensor system of the robotic device, a torque sensor system of the robotic device, or a combination thereof;
    evaluating the measured values and forwarding the evaluation to the medical imaging system, wherein the evaluated measured values comprise information on a movement of the region of interest, a position of the region of interest, or a combination thereof; and
    recording image data from the region of interest by the medical imaging system, wherein the evaluated measured values are used to actuate the medical imaging system,
    wherein the recording of the image data comprises an irradiation of the region of interest by the X-ray source and the recording of the irradiated region of interest by the X-ray detector, and
    wherein at least two projection recordings of the region of interest are recorded at a same time in each phase of successive phases of a cyclic movement of the region of interest.

2. The method of claim 1, wherein the irradiation of the region of interest and the recording of the image data is gated in dependence on the movement of the region of interest, positional data from the region of interest, or a combination thereof.

3. The method of claim 1, wherein at least one projection recording of the region of interest is recorded at a predetermined time in each phase of successive phases of the cyclic movement of the region of interest.

4. The method of claim 1, wherein the two projection recordings are recorded from different projection directions and used for 2D-2D-3D registration.

5. The method of claim 1, further comprising:
    processing the recorded image data using the evaluated measured values.

6. The method of claim 1, wherein the robotic device comprises an end effector at one end of the robotic device, wherein the end effector is configured to be in tactile contact with the patient.

7. The method of claim 6, wherein the end effector comprises a toothed sleeve configured to be in contact with a bone of the patient.

8. A method for recording image data of a moving region of interest of a patient by a medical imaging system comprising an X-ray source and an X-ray detector, the method comprising:
    positioning a robotic device having a kinematic chain of moving components against the patient to provide a tactile connection having a pressure against the patient, wherein the tactile connection is maintained for at least a prespecified period by force regulation and/or torque regulation;
    recording image data from the region of interest by the medical imaging system, wherein the recording of the image data comprises an irradiation of the region of interest by the X-ray source and the recording of the irradiated region of interest by the X-ray detector, and wherein at least two projection recordings of the region of interest are recorded at a same time in each phase of successive phases of a cyclic movement of the region of interest; and
    acquiring measured values by sensors of the robotic device positioned against the patient, wherein the measured values are acquired by a force sensor system of the robotic device, a torque sensor system of the robotic device, or a combination thereof,
    wherein the measured values are subsequently evaluated and forwarded to the medical imaging system, wherein the evaluated measured values comprise information on a movement of the region of interest, a position of the region of interest, or a combination thereof, and
    wherein the recorded image data is processed using the evaluated measured values.

9. A medical imaging system for an acquisition of image data of a cyclically moving region of interest of a patient, the medical imaging system comprising:
   an imaging unit comprising an X-ray source for emitting X-rays and an X-ray detector for recording image data from the region of interest of the patient, wherein at least two projection recordings of the region of interest are recorded at a same time in each phase of successive phases of a cyclic movement of the region of interest;
   a robotic device with a kinematic chain of moving components comprising a force sensor system, a torque sensor system, or a combination thereof for recording measured values comprising information on a movement of the region of interest, a position of the region of interest, or a combination thereof, wherein the robotic device is configured to have a tactile connection with a pressure against the patient, wherein the tactile connection is configured to be maintained for at least a prespecified period by force regulation and/or torque regulation;
   an evaluation unit for an evaluation of the measured values;
   a communication link for forwarding the measured values; and
   a control unit for a gated actuation of the recording of the image data,
   wherein the medical imaging system is configured to use the evaluated measured values to actuate the medical imaging system.

10. The medical imaging system of claim 9, wherein the control unit is configured for the gated actuation of a radiation output and the recording of image data.

11. The medical imaging system of claim 10, wherein the control unit is configured to control an irradiation of the region of interest and the recording of the image data gated in dependence on the evaluated measured values.

12. The medical imaging system of claim 10, further comprising:
   a registration unit for performing 2D-2D-3D registration between two 2D projection recordings recorded from different projection directions at the same time in each phase of the successive phases of the cyclic movement of the region of interest and a 3D volume image of the region of interest.

13. The medical imaging system of claim 9, further comprising:
   an image processing unit for processing the image data using the evaluated measured values.

* * * * *